(12) United States Patent
Some (10) Patent No.: US 7,433,053 B2
(45) Date of Patent: Oct. 7, 2008

(54) LASER INSPECTION USING DIFFRACTIVE ELEMENTS FOR ENHANCEMENT AND SUPPRESSION OF SURFACE FEATURES

(75) Inventor: Daniel Some, Ashdod (IL)

(73) Assignee: Applied Materials, Israel, Ltd., Rehovot (IL)

( * ) Notice: Subject to any disclaimer, the term of this patent is extended or adjusted under 35 U.S.C. 154(b) by 1065 days.

(21) Appl. No.: 10/215,943

(22) Filed: Aug. 8, 2002

(65) Prior Publication Data

US 2004/0027564 A1 Feb. 12, 2004

(51) Int. Cl.
*G01B 9/02* (2006.01)
(52) U.S. Cl. ..................................... 356/512
(58) Field of Classification Search ................ 356/499, 356/521, 488, 512
See application file for complete search history.

(56) References Cited

U.S. PATENT DOCUMENTS

| | | | |
|---|---|---|---|
| 4,731,855 A | 3/1988 | Suda et al. | |
| 5,463,459 A | * 10/1995 | Morioka et al. | 356/237.5 |
| 5,909,281 A | * 6/1999 | Bruning | 356/499 |
| 6,366,352 B1 | 4/2002 | Goldberg et al. | |

* cited by examiner

*Primary Examiner*—Hwa (Andrew) Lee
(74) *Attorney, Agent, or Firm*—Sughrue Mion PLLC (57) ABSTRACT

Apparatus for optical inspection of a sample includes a radiation source, adapted to irradiate a spot on the sample with coherent radiation, and collection optics, adapted to collect the radiation scattered from the spot so as to form a beam of scattered radiation. A diffractive optical element (DOE) is positioned to intercept the beam of scattered radiation and is adapted to deflect a first portion of the beam by a predetermined offset relative to a second portion of the beam, and then to optically combine the first portion with the second portion to generate a product beam. A detector is positioned to receive the product beam and to generate a signal responsive thereto, which is processed by a signal processor so as to determine an autocorrelation value of the product beam.

50 Claims, 7 Drawing Sheets

FIG. 7

LASER INSPECTION USING DIFFRACTIVE ELEMENTS FOR ENHANCEMENT AND SUPPRESSION OF SURFACE FEATURES

FIELD OF THE INVENTION

The present invention relates generally to optical inspection systems, and specifically to methods and systems for detecting defects on substrates.

BACKGROUND OF THE INVENTION

Laser scanning systems are well known in the art of optical inspection. Such systems are used particularly for detection of defects on substrates, such as both patterned and unpatterned semiconductor wafers. As the laser beam is scanned over the surface of the substrate, the radiation scattered from the surface is measured, typically using an array of optical detectors. Defects on the surface, such as foreign particles and scratches, generally scatter more strongly than clean, flat surfaces, and can thus be located and identified on unpatterned substrates simply on the basis of their scatter. On the other hand, if the surface is patterned, light typically scatters not only from defects, but also from features of the pattern itself. A variety of methods have therefore been developed for distinguishing scattered light due to defects from background scatter arising from the pattern.

Some types of features scatter light with a distinctive spatial signature. For example, long, narrow features, such as metal lines, grooves and some polycrystalline grain boundaries, scatter preferentially in a narrow angular band perpendicular to the scattering feature. As another example, square corners in a pattern tend to scatter in two preferred directions, separated by 90°. A variety of different feature types and their characteristic scattering patterns are described in U.S. Pat. No. 4,731,855, whose disclosure is incorporated herein by reference. In the system described in this patent, defects on a surface are identified by scanning the surface with a laser beam at normal incidence, and then detecting scattered light using an array of detectors positioned at different angles. The pattern of the scattered light is processed in order to discriminate between the characteristic, normal scattering patterns of desired surface features and abnormal scattering due to defects. In other defect detection systems, an image is formed of light scattered from the surface. The image is then processed to separate the defects from the background scattering.

In the course of inspecting a substrate such as a semiconductor wafer at high resolution, a very large volume of scattering data is collected. Substantial computing resources are required to process all these data digitally in order to separate defect signals from background scatter, as is performed in systems known in the art. Furthermore, when the background scatter is strong, it can overwhelm weak scattering signals from faint defects. There are methods known in the art for enhancing or suppressing features on the wafer by spatial filtering. An exemplary method is described in U.S. Pat. No. 6,366,352, whose disclosure is incorporated herein by reference. Such methods, however, are generally incapable of filtering out randomly-oriented features, and are useful only for those features having a fixed and predetermined orientation on the substrate.

SUMMARY OF THE INVENTION

It is an object of some aspects of the present invention to provide improved systems and methods for optical inspection of substrates, particularly of patterned substrates, such as semiconductor wafers in the process of manufacture.

It is a further object of some aspects of the present invention to provide devices and methods for optically suppressing background scatter in laser-based substrate inspection.

It is still a further object of some aspects of the present invention to provide devices and methods for enhancing scattering signals due to certain features of interest.

In preferred embodiments of the present invention, a laser beam is scanned over a surface under inspection, and radiation scattered from the surface is collected and collimated by an collection optics. A diffractive optical element (DOE) performs an optical autocorrelation operation on the beam of scattered radiation. In this operation, a portion of the beam is offset by a predetermined angle and then combined with the original scattered beam. The offset angle is preferably chosen so that the autocorrelation suppresses scatter from certain types of surface features, such as linear features. Alternatively or additionally, the offset angle may be chosen so as to enhance scatter from certain feature or defect types. Further alternatively or additionally, the offset angle may be chosen so as to enhance or suppress scatter from features or defects that are located at the surface or at a certain depth relative to the surface.

The beam of scattered radiation that has been optically processed by the DOE is received by a detector. The detector output signal is then processed in order to characterize the surface, typically so as to locate and classify defects on the surface. Preferably, for this purpose a reference beam of the scattered radiation is split off and detected, without being processed by the DOE. The difference between the detector signals from the filtered and reference beams gives a measure of the autocorrelation of the scattered radiation for the selected offset angle.

The methods of the present invention are particularly suited for inspecting surfaces of substrates that are patterned with small features. Examples of such substrates include semiconductor wafers, printed circuit boards, and other elements used in microelectronic manufacturing processes. In these applications, the DOE is preferably chosen so as to suppress radiation scattered from known surface features, so as to facilitate detection of abnormal scatter due to defects. Alternatively, the methods of the present invention may be used to enhance scattering from certain defects, such as scratches, that may occur on unpatterned surfaces, such as bare or blanket semiconductor wafers, or optical elements. Other applications of the principles of the present invention will be apparent to those skilled in the art and are considered to be within the scope of the present invention.

There is therefore provided, in accordance with a preferred embodiment of the present invention, apparatus for optical inspection of a sample, including:

a radiation source, adapted to irradiate a spot on the sample with coherent radiation;

collection optics, adapted to collect the radiation scattered from the spot so as to form a beam of scattered radiation;

a diffractive optical element (DOE), which is positioned to intercept the beam of scattered radiation and is adapted to deflect a first portion of the beam by a predetermined offset relative to a second portion of the beam, and then to optically combine the first portion with the second portion to generate a product beam;

a detector, positioned to receive the product beam and to generate a signal responsive thereto; and a signal processor, which is coupled to receive and process the signal from the detector so as to determine an autocorrelation value of the product beam.

Preferably, the collection optics include dark-field optics, so that the radiation that is reflected specularly from the sample is not incident on the DOE. Most preferably, the coherent radiation is incident on the spot in a direction approximately normal to a surface of the sample, and the collection optics are configured to form the beam of scattered radiation so that the beam is collimated with an annular cross-section.

Alternatively, the collection optics are adapted to collect the radiation scattered from the spot at a grazing angle relative to a surface of the sample.

Preferably, the DOE includes a first diffractive component, having a first grating formed thereon, such that the first and second portions of the beam correspond to different diffraction orders of the grating. Most preferably, the first portion of the beam includes a first diffraction order of the grating, while the second portion of the beam includes a zero diffraction order of the grating. Typically, the DOE further includes a second diffractive component, having a second grating formed thereon, so as to direct at least parts of the first and second portions of the beam in a common direction. Preferably, the second diffractive component is adapted and positioned, relative to the first diffractive component, so that the parts of the first and second portions of the beam that are directed in the common direction add together in phase. In a preferred embodiment, the DOE includes focusing optics, which are adapted to focus the portions of the beam that add together in phase onto the detector, and a beam stop, which is configured to block further portions of the beam that add together in antiphase from impinging on the detector.

In a preferred embodiment, the first grating includes a linear grating. In another preferred embodiment, the first grating includes an array of concentric rings.

In a preferred embodiment, the first grating is adapted to deflect the first portion of the beam that is incident on the DOE at an azimuthal angle $\phi$ so that it is optically combined with the second portion of the beam that is incident at a further azimuthal angle $\phi+\Delta\phi$, such that $\Delta\phi$ is substantially fixed over all azimuthal angles $\phi$.

In a further preferred embodiment, the first diffractive component has a thickness that varies over an area thereof, so as to impart a variable phase delay to the beam of scattered radiation that is incident over the area.

Preferably, the detector includes a first detector, and the signal generated thereby includes a first signal, and the apparatus includes a second detector, positioned to receive a part of the beam of scattered radiation not intercepted by the DOE and to generate a second signal responsive to the part of the beam that it receives, wherein the signal processor is adapted to receive and compare the first and second signals in order to determine the autocorrelation value.

In some preferred embodiments of the present invention, the DOE is arranged so that a contribution to the scattered radiation due to a linear feature on the sample is suppressed in the product beam or, alternatively, is enhanced in the product beam.

In further preferred embodiments of the present invention, the DOE is arranged so that a contribution to the scattered radiation due to a first feature located on a surface of the sample is enhanced in the product beam relative to the scattered radiation due to a second feature buried below the surface or, alternatively, so that a contribution to the scattered radiation due to a defect on a surface of the sample is enhanced in the product beam. In still another preferred embodiment, the DOE is arranged so that a contribution to the scattered radiation due to a corner on the sample is suppressed in the product beam.

Preferably, the apparatus includes a scanning device, which is adapted to cause the irradiated spot to scan over a region of the sample, so as to enable the signal processor to determine the autocorrelation value at multiple points in the region. In a preferred embodiment, the signal processor is adapted to identify defects on the sample responsive to the autocorrelation value.

There is also provided, in accordance with a preferred embodiment of the present invention, a method for optical inspection of a sample, including:

irradiating a spot on the sample with coherent radiation;

collecting the radiation scattered from the spot so as to form a beam of scattered radiation;

positioning a diffractive optical element (DOE) to intercept the beam of scattered radiation, so as to deflect a first portion of the beam by a predetermined offset relative to a second portion of the beam, and then to optically combine the first portion with the second portion to generate a product beam;

receiving the product beam and generating a signal responsive thereto; and processing the signal from the detector so as to determine an autocorrelation value of the product beam.

There is additionally provided, in accordance with a preferred embodiment of the present invention, an optical element, for processing a beam of radiation, the element including:

a first diffractive component, having a first grating formed thereon, which is adapted to diffract a first portion of the beam by a predetermined offset relative to a second portion of the beam; and a second diffractive component, having a second grating formed thereon, which is positioned to intercept the first and second portions of the beam and to diffract at least parts of the first and second portions in a common direction so as to combine the at least parts of the first and second portions into a product beam.

Preferably, the first portion of the beam includes a first diffraction order of the first grating, while the second portion of the beam includes a zero diffraction order of the first grating.

Further preferably, the second diffractive component is adapted and positioned, relative to the first diffractive component, so that the at least parts of the first and second portions of the beam that are diffracted in the common direction add together in phase. Most preferably, the optical element includes focusing optics, which are adapted to focus the portions of the beam that add together in phase, and a beam stop, which is configured to block further portions of the beam that add together in antiphase.

In a preferred embodiment, the predetermined offset includes an azimuthal offset. Preferably, the first grating is adapted to diffract the first portion of the beam that is incident on the DOE at an azimuthal angle $\phi$ such that the first portion is coincident on the second grating with the second portion of the beam that is incident on the first grating at a further azimuthal angle $\phi+\Delta\phi$, such that $\Delta\phi$ is substantially fixed over all azimuthal angles $\phi$.

In another preferred embodiment, the predetermined offset includes a radial offset. In still another preferred embodiment, the first diffractive component has a thickness that varies over an area thereof, so as to impart a phase delay to the beam of radiation that is variable over the area.

Preferably, the product beam corresponds to an autocorrelation of the beam of radiation subject to the predetermined offset.

The present invention will be more fully understood from the following detailed description of the preferred embodiments thereof, taken together with the drawings in which:

DETAILED DESCRIPTION OF PREFERRED EMBODIMENTS

Figure 1:
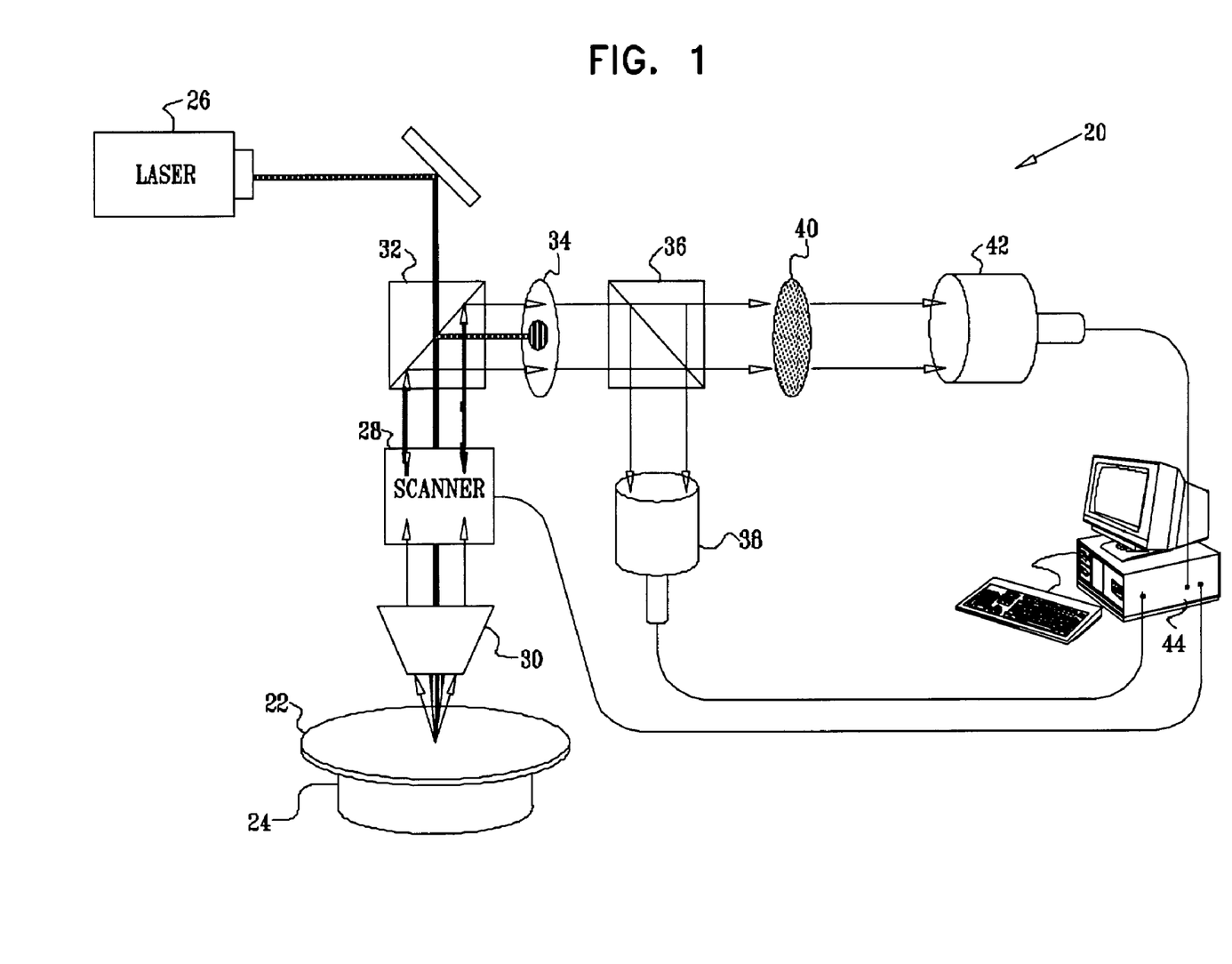
FIG. 1 is a schematic side view of a system for optical inspection, in accordance with a preferred embodiment of the present invention.

FIG. 1 is a schematic side view of a system 20 for optical inspection of a substrate 22, in accordance with a preferred embodiment of the present invention. Substrate 22, typically a semiconductor wafer, is mounted on a stage 24. A laser source 26 generates a collimated beam of coherent radiation, which is scanned over the surface of substrate 22 by a scanner 28, such as a rotating polygon or galvanometric scanning mirror. Alternatively or additionally, stage 24 may be translated and/or rotated so that the substrate moves relative to the laser beam. The surface of substrate may thus be scanned by the laser beam using substantially any combination of optical scanning by scanner 28 and mechanical motion by stage 24, or by optical scanning alone or mechanical scanning (rotation and/or translation) alone. Typically, laser source 26 emits visible light, but an ultraviolet or infrared radiation source may be used for this purpose, as well.

The radiation from laser source 26 is focused onto substrate 22 by an objective 30, which also collects and collimates the resulting scattered radiation. Preferably, the diameter of the incident laser beam is such that it fills only a small part of the entrance pupil of the objective, as shown in the figure. The remainder of the pupil of the objective then defines an annular dark-field region, collecting only scattered and diffracted radiation from the surface of the substrate, without specular components.

The beam of scattered radiation formed by objective 30 is separated from the incident beam by a beamsplitter 32. A filter 34 with a central stop blocks specular reflection from the substrate, so that the scattered beam is collimated with an annular cross-section. Alternatively, an annular mirror may be used in place of these two elements. A further beamsplitter 36 picks off a portion of the scattered beam and directs it toward a reference detector 38, which is used to measure the total intensity of the scattered radiation, $I_0$. The remainder of the scattered beam is intercepted by a diffractive optical element (DOE) 40, which performs an autocorrelation operation on the scattered beam as described in detail hereinbelow. Depending on the form and configuration of DOE 40, the autocorrelation operation may serve either to suppress or to enhance characteristic scatter from features or defects of certain types on substrate 22. An autocorrelation detector 42 receives the beam that has been processed by DOE 40 and now includes an autocorrelation component. Detectors 38 and 42 typically comprise photomultiplier tubes or high-sensitivity optical detectors of other types, as are known in the art.

For proper operation of DOE 40, it is desirable that the collimated beam of scattered radiation remain substantially centered on the DOE, and that its angle of incidence on the DOE be substantially constant. This condition may be satisfied, for example, by using a rotating polygon mirror to scan the laser beam over substrate 22, if the same polygon is also used to direct the scattered beam toward DOE 40 (thereby canceling out the angular offset introduced by the polygon). Alternatively, the condition is met if the scanning is accomplished solely by means of stage 24, without deflecting the laser beam. Other optical configurations operable with DOE 40 will be apparent to those skilled in the art.

A signal processor 44, typically a general-purpose computer with suitable input circuits and software, processes the signals from detectors 38 and 42. Processor 44 analyzes the difference between the signals from the two detectors, as described in greater detail hereinbelow, in order to extract and measure the autocorrelation component of the scattered beam generated by DOE 40. Processor 44 typically tracks the value of the autocorrelation component as the laser beam scans the substrate in order to identify and classify defects on the substrate surface. After the autocorrelation component has been extracted from the scattering signals, substantially any suitable processing method may be applied to this signal component for the purpose of surface inspection, for example, threshold detection or die-to-die comparison, as are known in the art.

Although objective 30 and DOE 40 are shown in FIG. 1 as comprising transmissive optical components, the functions of these optical element may also be performed by reflective components, as long as appropriate changes are made to the optical paths shown in the figure. Typically, reflective diffractive components can be produced simply by applying a reflective coating to the rear surface of a diffractive element.

Figure 2A:
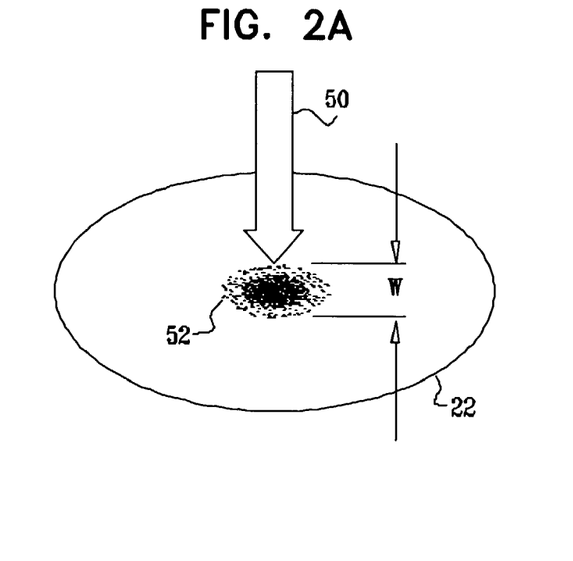
FIG. 2A is a schematic, pictorial illustration showing incidence of a laser beam on a substrate.
Figure 2B:
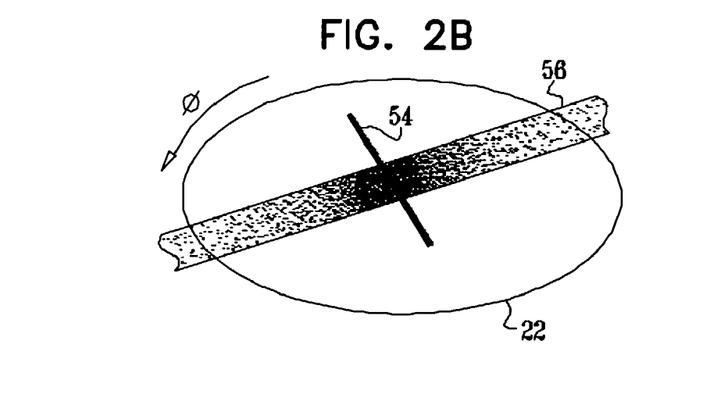
FIGS. 2B and 2C are schematic, pictorial illustrations showing typical patterns of scattered radiation due to incidence of the beam of FIG. 2A on different features of the substrate.
Figure 2C:
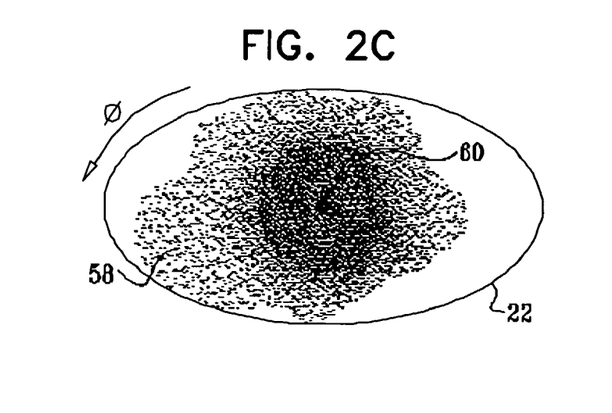

Reference is now made to FIGS. 2A, 2B and 2C, in order to describe the rationale behind the use of DOE 40 to suppress scatter signals from linear features on substrate 22. FIG. 2A illustrates a laser beam 50 incident on substrate 22. The beam forms a spot 52 on the surface of the substrate with a diameter W, determined by the beam diameter.

FIG. 2B schematically illustrates a characteristic pattern 56 of scattering of the laser beam from a linear feature 54 on substrate 22. Feature 54 may comprise, for example, a metal line, a scratch or a large polycrystalline grain boundary on a semiconductor wafer. Pattern 56 appears as a bright band passing across the center of the dark-field collection annulus, from one side to the other. This band is perpendicular to feature 54, and the width of the band is approximately equal to the width of the beam entering the pupil of objective 30.

FIG. 2C shows a scattering pattern 58 generated by an arbitrary point defect 60. Typically, pattern 58 does not have a clearly-preferred direction of scattering and is spread over a larger portion of the dark-field annulus than pattern 56. Assuming feature 54 and defect 60 are located in mutual proximity on substrate 22, and the object of system 20 is to detect defect 60, it is desirable to suppress radiation in pattern 56 without substantially attenuating pattern 58. This object is achieved using DOE 40.

In order to suppress pattern 56, DOE 40 performs an optical autocorrelation over the dark-field annulus that gives the result:

$$I_{ac}(\Delta\phi) = k \int |E(\phi)E(\phi+\Delta\phi)| d\phi \tag{1}$$

Here $\phi$ is the azimuthal angle around the detection annulus, as marked in FIGS. 2B and 2C, and k is a constant. $E(\phi)$ is the field of the scattered light at angle $\phi$, which is assumed to have constant phase over the annulus. The shift angle $\Delta\phi$ is set to a fixed value between 0 and 180°, preferably in the range between 20 and 50°. The value of $\Delta\phi$ is most preferably chosen to be large enough so that there is no overlap between the different diffraction orders of the scattered radiation at angles separated $\Delta\phi$. Proper choice of $\Delta\phi$ will cause $I_{ac}(\Delta\phi)$ to be near zero for pattern 56, while $I_{ac}(\Delta\phi)$ for pattern 58 will be non-zero substantially irrespective of the value chosen for $\Delta\phi$.

Figure 3:
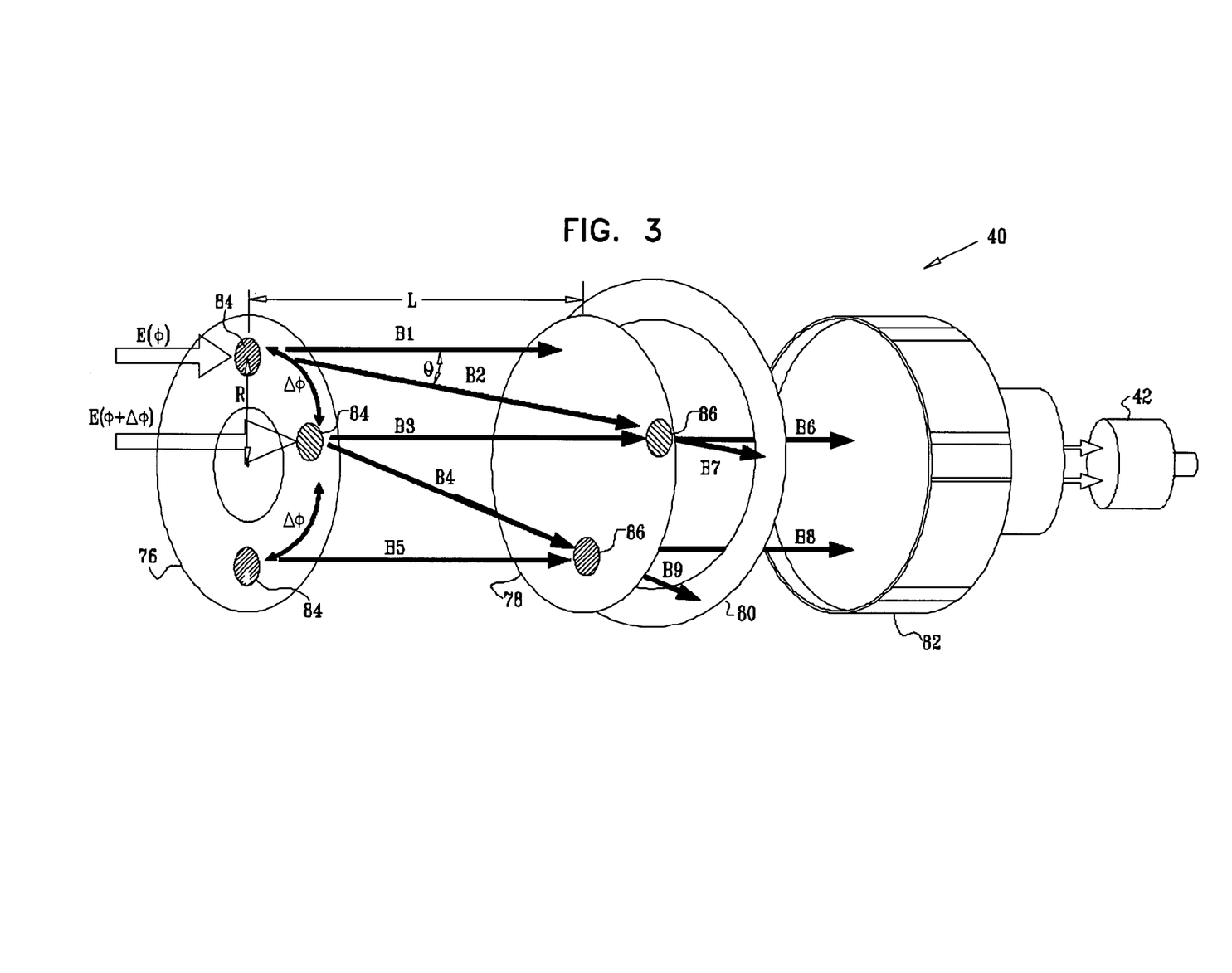
FIG. 3 is a schematic, pictorial illustration showing details of a diffractive optical element (DOE), in accordance with a preferred embodiment of the present invention.

FIG. 3 is a schematic, pictorial view of DOE 40, which is designed to implement the autocorrelation function of equation (1), in accordance with a preferred embodiment of the present invention. DOE 40 comprises first and second diffractive components 76 and 78, separated by a spacing L. The diffractive components are followed by an annular beam stop 80 and a telescope 82, which reduces the beam diameter of the light filtered by DOE 40 and directs the light onto detector 42 while maintaining collimation. Components 76 and 78 comprise phase gratings 84 and 86, respectively, which may be formed by any suitable means known in the art, such as optical or electron beam lithography. In particular, multi-level lithography may be used to create a three-dimensional, blazed grating profile with characteristics such as grating depth, blaze angle, shape and refractive index chosen so as to diffract the incident light preferentially into certain orders, preferably the zero and first orders, while suppressing other orders. Gratings produced by multi-level lithography are available, for example, from Rochester Photonics (Rochester, N.Y.). Typically, the phase gratings extend over the entire active surfaces of components 76 and 78. Only small areas of the gratings are shown in this figure, however, in order to clarify the operational principles of DOE 40.

At each point on component 76, grating 84 splits the incident beam of scattered radiation into a zero-order portion, which passes straight through component 76, and a first-order portion. The zero-order rays shown in the figure are labeled B1, B3 and B5, while the first-order rays are labeled B2 and B4. The first-order rays exit component 76 at a diffraction angle $\theta$ such that the first-order ray from any azimuth $\phi$ will intersect with the zero-order ray from azimuth $\phi+\Delta\phi$ at component 78. To satisfy this condition, it is necessary that at a radial distance R from the center of component 76, the diffraction angle $\theta$ is given by:

$$\tan(\theta) = \frac{L}{2R\sin(\Delta\phi/2)} \tag{2}$$

For a given laser wavelength $\lambda$, the grating period d is given by:

$$\sin(\theta) = \lambda/d \tag{3}$$

At any point $(R,\phi)$ on component 76, the lines of grating 84 should be oriented perpendicular to a line directed from $(R,\phi)$ to $(R,\phi+\Delta\phi)$, so that the zero- and first-order rays of $E(R,\phi)$ and $E(R,\phi+\Delta\phi)$ intersect at the proper point.

Grating 86 operates in a complementary manner to grating 84, so as to combine these first- and zero-order rays into in-phase sums B6 and B8, and anti-phase sums B7 and B9. Beam stop 80 blocks the anti-phase sums, while lens 82 focuses the in-phase sums onto detector 42. The in-phase sums interfere at detector 42, to give the following intensity component for each azimuth $\phi$:

$$I_{det}(\phi, \Delta\phi) = k|\alpha E(\phi) + \beta E(\phi + \Delta\phi)e^{i\delta}|^2 \tag{4}$$

Here $\alpha$ and $\beta$ are the relative fractions of the field E of the incident beam that are transmitted by grating 84 into the first- and zero-order rays, respectively. The difference in optical path length of the two rays from component 76 to component 78 gives a phase difference of $\delta$.

Detector 42 effectively integrates the intensity components of equation (4) over all $\phi$ to give the following total intensity signal:

$$\begin{aligned} I_{det}(\Delta\phi) &= k \int |\alpha E(\phi) + \beta E(\phi + \Delta\phi)e^{i\delta}|^2 d\phi \\ &= k \int (\alpha^2 |E(\phi)|^2 + \beta^2 |E(\phi + \Delta\phi)|^2 + \\ &\quad 2\alpha\beta |E(\phi)E(\phi + \Delta\phi)|\cos(\delta)) d\phi \\ &= (\alpha^2 + \beta^2)I_0 + 2\alpha\beta I_{ac}(\Delta\phi)\cos(\delta) \end{aligned} \tag{5}$$

The value of $I_0$ is provided by reference detector 38 (FIG. 1), to within the constant value $(\alpha^2+\beta^2)$, which can be determined by calibration. $\delta$ is a constant given by:

$$\delta = \frac{2\pi}{\lambda}\left(\sqrt{L^2 + (2R(\sin(\Delta\phi/2))^2} - L\right) \tag{6}$$

Preferably, the values of L and $\theta$ are chosen so that $\cos(\delta)$ is equal to one. After suitable calibration and normalization, processor 44 simply subtracts the signal values received from detectors 38 and 42 to determine $I_{ac}$. This signal value is indicative of scattering from the spot on which the laser beam is incident on substrate 22, less any scattering component due to a linear feature on the substrate that may fall within the spot.

Alternatively, DOE 40 as defined above may be used to enhance the signal received by detector 42 due to scattering from linear features on substrate 22. For this purpose, $\Delta\phi$ is set to 180°, so that gratings 84 and 86 are made up of concentric rings with period d given by the equations above. This alternative embodiment is particularly useful, for example, in detecting scratches on smooth or textured substrates.

Figure 4A:
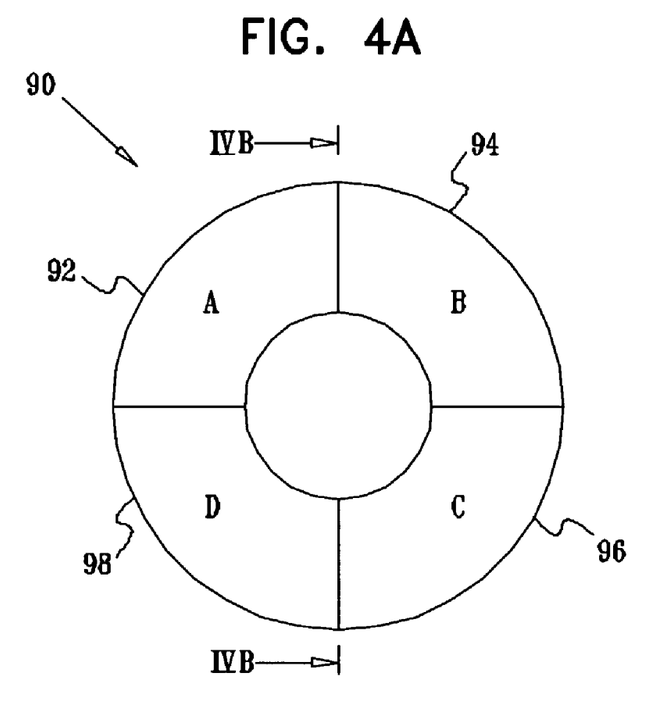
FIG. 4A is a schematic front view of a diffractive optical component, in accordance with a preferred embodiment of the present invention.
Figure 4B:
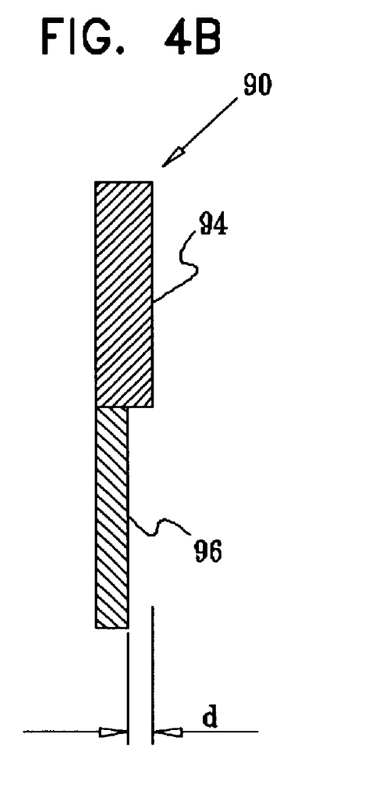
FIG. 4B is a schematic, sectional illustration of the component of FIG. 4A.

FIGS. 4A and 4B schematically illustrate another diffractive component 90 for enhancing scattering signals due to linear features, in accordance with a preferred embodiment of the present invention. Component 90 is shown in front view in FIG. 4A and in a sectional view in FIG. 4B. This component can be used, for example, in place of component 76 in DOE 40.

A grating (not shown in this figure) is formed on the surface of component 90. The grating typically comprises concentric rings, as described above, so as to correlate the incident field for $\Delta\phi=180°$. In addition, to suppress scattering due to particles and right-angle features, such as corners, component 90 is divided into four quadrants 92, 94, 96 and 98, labeled A, B, C and D, respectively. Quadrant 94 is made thicker than the other quadrants by a difference d, which is chosen so as to introduce an extra half-wave delay into rays of the scattered radiation passing through this quadrant, relative to the other quadrants. Typically, for visible light, given a refractive index n=1.5 for component 90, d is approximately 3 mm.

To understand the rationale for this design of the DOE, let A, B, C and D represent the intensities of scattered radiation incident on component 90 in the respective quadrants. If all the quadrants were of the same thickness, DOE 40 using this component would generate an autocorrelation that can be expressed schematically as AxC+BxD. Introducing the extra half-wave delay in quadrant 94, however, changes the autocorrelation output to AxC−BxD. In other words, for scatter in quadrants A and C, $\cos(\delta)=1$, while in quadrants B and D, $\cos(\delta)=-1$. Typically, for linear features, A=C≠B=D, so that component 90 will continue to enhance the autocorrelation signal due to this type of scattering (except for features that are perfectly aligned along the horizontal or vertical axis of the DOE—which typically correspond to intentional patterns on the inspected substrate). For scatter from particles, on the other hand, as shown in FIG. 2C, it is typical that A=B=C=D. Therefore, the output AxC−BxD will cancel to zero. Similarly, for right-angle features, the scatter into each of two pairs of mutually-adjacent quadrants will typically be roughly equal, for example, A=B≠C=D. In this case, too, AxC−BxD cancels to zero. Thus, component 90 enhances the scatter autocorrelation signal due to linear features, such as scratches, relative to other types of scatterers.

Figure 5A:
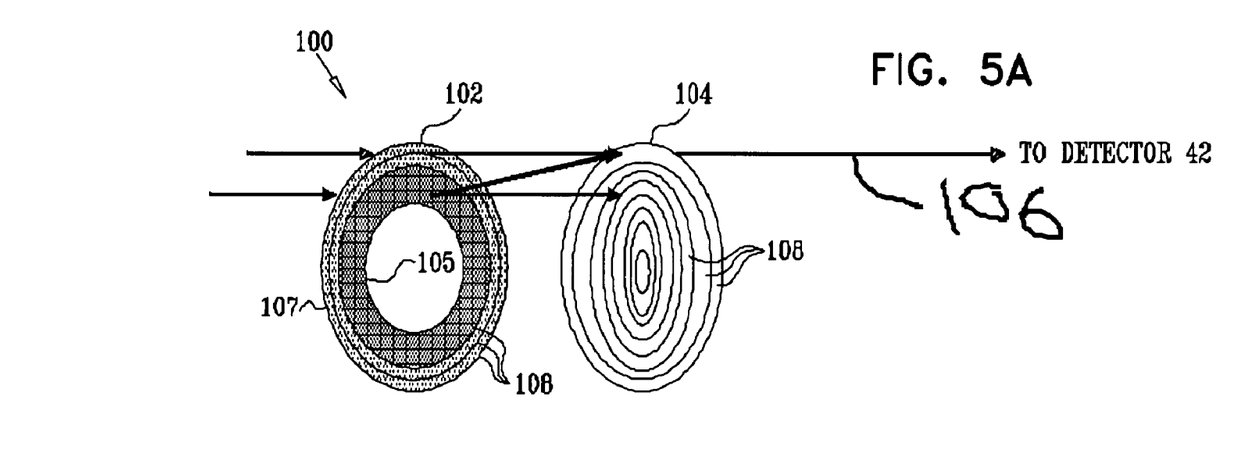
FIG. 5A is a schematic, pictorial illustration showing a DOE used for enhancing radiation scattered from a particle at the surface of a substrate, in accordance with a preferred embodiment of the present invention.
Figure 5B:
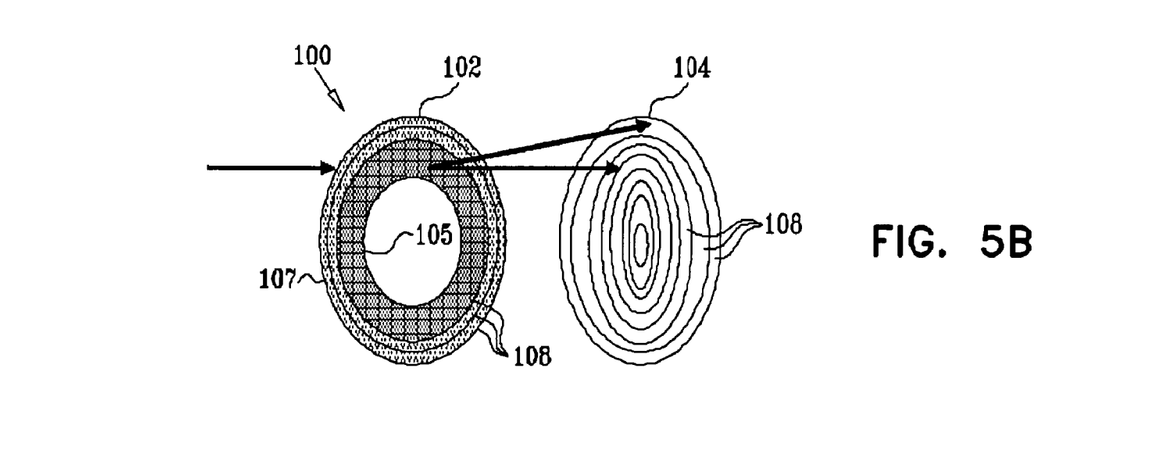
FIG. 5B is a schematic, pictorial illustration showing suppression of radiation scattered from a particle at a depth within the substrate by the DOE of FIG. 5A.

FIGS. 5A and 5B schematically illustrate a DOE 100 that can be used in system 20, for example, in accordance with another preferred embodiment of the present invention. DOE 100 can be used to enhance the scatter signal due to features on the surface of substrate 22, such as surface defects, relative to scatterers buried in the substrate. Typically, surface features scatter into a wide range of elevation angles, while buried features scatter preferentially into high elevations, i.e., angles closer to the normal to the surface. In other words, a particle on the surface of substrate 22 will typically scatter into a wide cone, while the scattering cone due to a buried defect will be substantially narrower. DOE 100 takes advantage of this distinction.

DOE 100 comprises first and second diffractive components 102 and 104, both of which have gratings 108 made up of concentric rings formed thereon. (The beamstop and telescope shown in FIG. 3 are omitted here for the sake of simplicity.) Rather than operating on the incident beam as a function of azimuth $\phi$, as in the preceding embodiments, the grating of component 102 generates a first-order diffracted beam that is deflected radially, away from the axis of DOE 100, as a function of scattering elevation. The spacing of gratings 108 and separation of components 102 and 104 are such as to correlate the scatter incident on an inner radial region 105 of component 102 with that incident on an outer radial region 107.

FIG. 5A shows an exemplary case in which radiation is scattered in a wide cone from a defect on the surface of substrate 22. After collimation by objective 30, the scattered radiation is incident on DOE 100 over a correspondingly wide radial range, i.e., on both of regions 105 and 107. In this case, a substantial autocorrelation beam 106 will reach sensor 42. By contrast, FIG. 5B shows a case of scattering from a buried defect into a narrow cone. As a result, the collimated beam of scattered radiation is incident only on inner region 105, so that the autocorrelation beam is much weaker.

Figure 6:
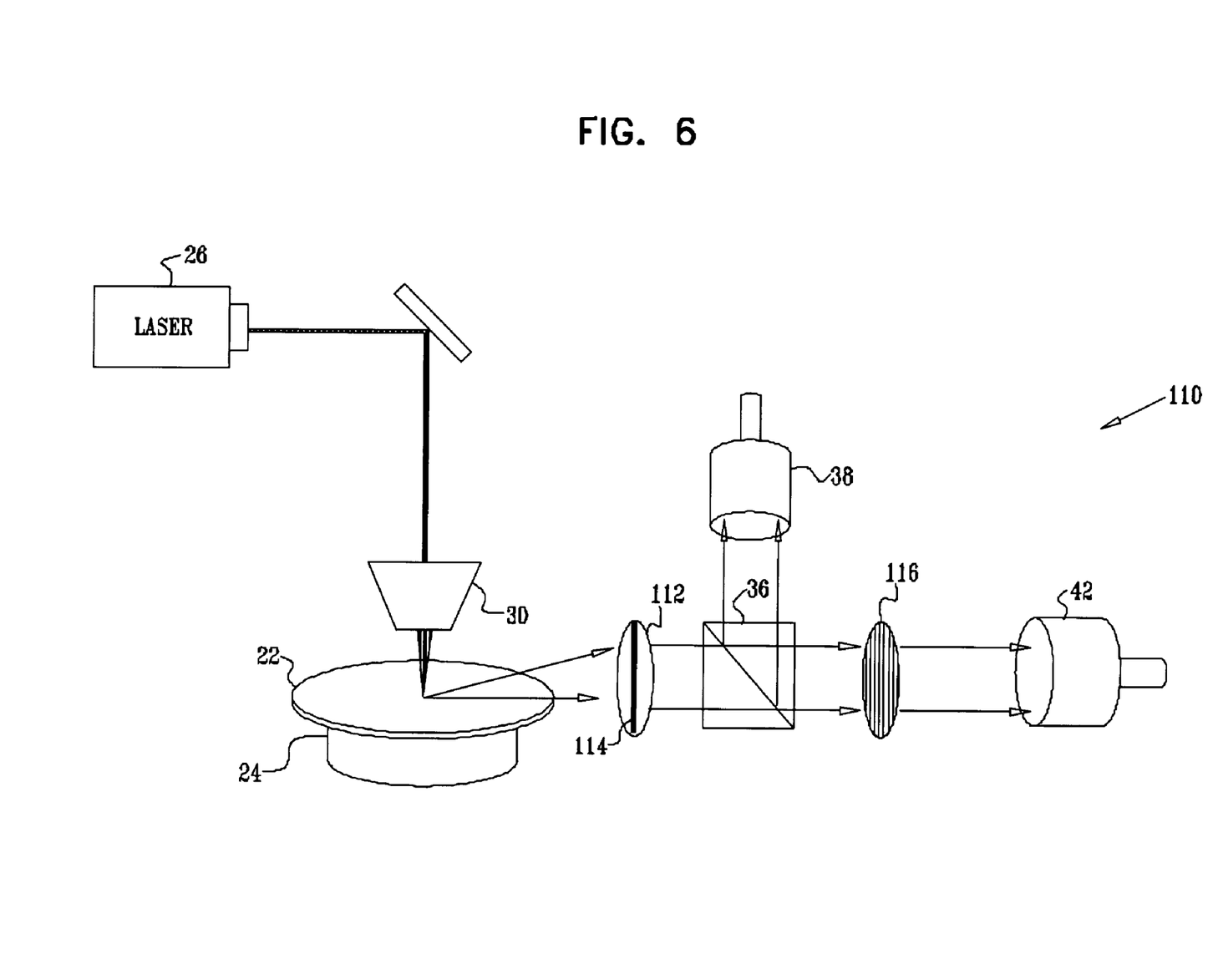
FIG. 6 is a schematic side view of a system for optical inspection, in accordance with another preferred embodiment of the present invention.

FIG. 6 is a schematic side view of a system 110 for optical inspection of substrate 22, in accordance with another preferred embodiment of the present invention. In this embodiment, while the beam from laser source 26 is still incident on substrate 22 in a direction normal to the surface, detectors 38 and 42 are positioned to capture radiation scattered at grazing angles. At these low scattering angles, the scatter pattern from a linear feature on the surface of the substrate has the form of a vertical band 114. (The entire pattern of scatter from such a linear feature corresponds to a line of longitude on an imaginary hemisphere above the substrate plane, which is centered on the point at which the laser beam is incident on the substrate. Band 114 is the bottom portion of this line of longitude.)

The grazing-angle scattered radiation is collected and collimated by a Fourier lens 112, instead of by objective 30. In order to suppress the scattered radiation in band 114, a DOE 116 comprises a simple linear grating, made up of vertically-oriented grating lines. The grating period is chosen so that the DOE generates an autocorrelation between regions of the scattered beam that are displaced horizontally one from another by a distance wider than band 114. The operational result is similar to that obtained using DOE 40, as described above.

Figure 7:
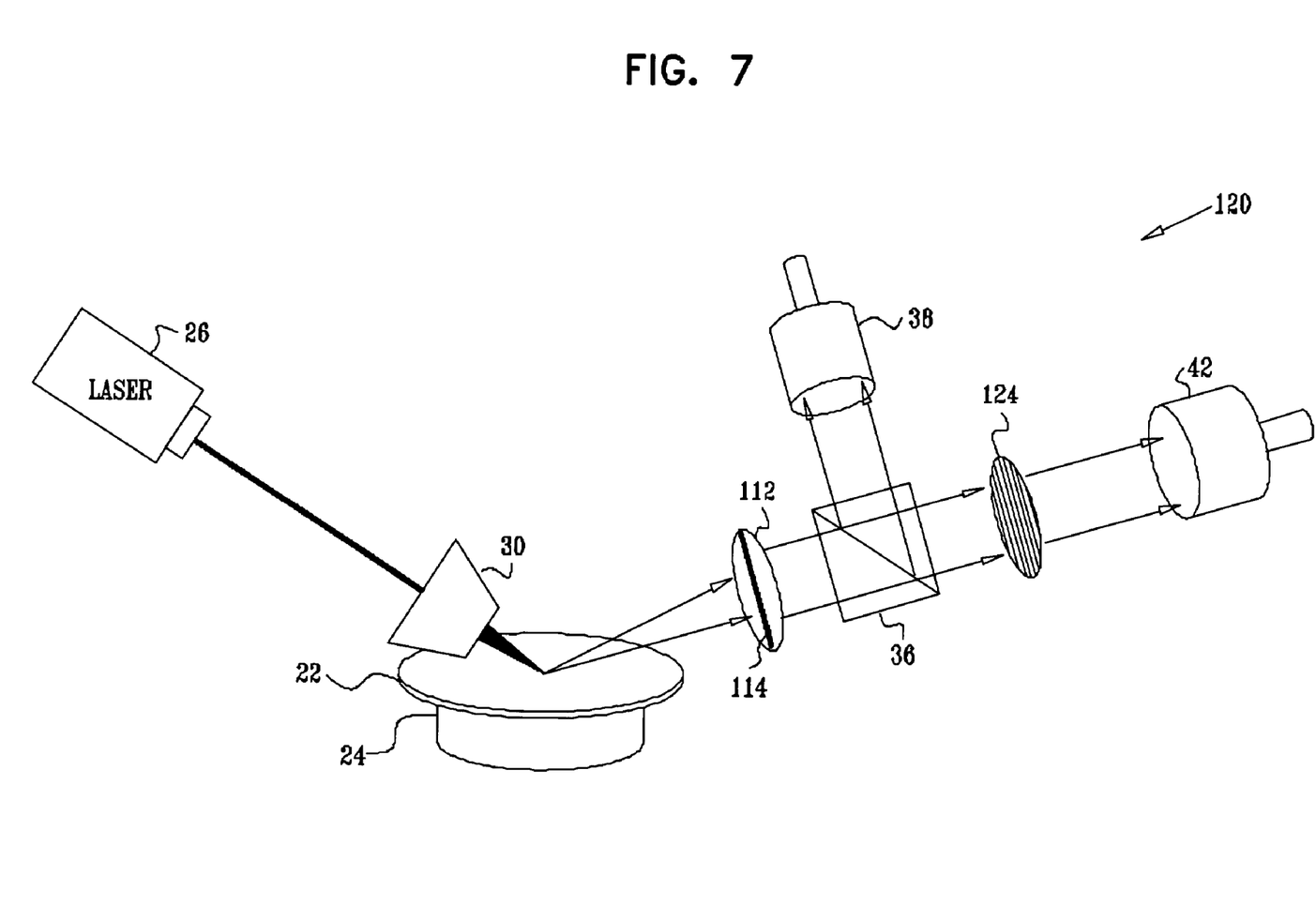
FIG. 7 is a schematic side view of a system for optical inspection, in accordance with still another preferred embodiment of the present invention.

FIG. 7 is a schematic side view of a system 120 for optical inspection of substrate 22, in accordance with yet another preferred embodiment of the present invention. In this embodiment, suitable optics are used so that the beam from laser source 26 is incident on the substrate surface at an oblique angle. (Scanning is preferably accomplished by rotation and/or translation of stage 24.) At this angle, the characteristic spatial signatures of features on the surface, such as band 114, still follow the same general principles as those described above with respect to normal-incidence scanning. Thus, for example, a DOE 124, similar to DOE 116 shown in FIG. 6, may be used in system 120 to suppress scattering from linear features on the surface. Alternatively, a DOE with an annular configuration, similar to that shown in FIG. 3, may be used to process the beam reflected from substrate 22. By the same token, while using oblique-angle irradiation as shown in FIG. 7, the scattered radiation may alternatively be collected in a direction normal to the surface. In this case, diffractive elements such as DOE 40 may be used for scattering enhancement and suppression, substantially as described above.

Although the preferred embodiments described above use certain particular optical configurations and relate to suppression and enhancement of scattering due to certain specific feature types, the principles of the present invention may likewise be applied in other optical configurations and adapted to other types of scattering features. Furthermore, although these preferred embodiments are drawn to applications in the field of optical inspection of substrates, the principles of optical autocorrelation taught by the present invention may also be used in other areas of optical imaging and signal processing.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for optical inspection of a sample, comprising:
   a radiation source, adapted to irradiate a spot on the sample with coherent radiation;
   dark field collection optics, adapted to collect the radiation scattered from the spot so as to form a beam of scattered radiation;
   a diffractive optical element (DOE), which is positioned to intercept the beam of scattered radiation and is adapted to deflect a first portion of the beam by a predetermined offset relative to a second portion of the beam, and then to optically combine the first portion with the second portion to generate a product beam;
   a detector, positioned to receive the product beam and to generate a signal responsive thereto; and
   a signal processor, which is coupled to receive and process the signal from the detector so as to determine an autocorrelation value of the product beam.

2. Apparatus according to claim 1, wherein the coherent radiation is incident on the spot in a direction approximately normal to a surface of the sample, and wherein the collection optics are configured to form the beam of scattered radiation so that the beam is collimated with an annular cross-section.

3. Apparatus according to claim 1, wherein the collection optics are adapted to collect the radiation scattered from the spot at a gazing angle relative to a surface of the sample.

4. Apparatus according to claim 1, wherein the DOE comprises a first diffractive component having a first grating formed thereon, such that the first and second portions of the beam correspond to different diffraction orders of the grating.

5. Apparatus according to claim 4, wherein the first portion of the beam comprises a first diffraction order of the grating, while the second portion of the beam comprises a zero diffraction order of the grating.

6. Apparatus according to claim 4, wherein the DOE further comprises a second diffractive component, having a second grating formed thereon, so as to direct at least parts of the first and second portions of the beam in a common direction.

7. Apparatus according to claim 6, wherein the second diffractive component is adapted and positioned, relative to the first diffractive component, so that the parts of the first and second portions of the beam that are directed in the common direction add together in phase.

8. Apparatus according to claim 7, wherein the DOE comprises focusing optics, which are adapted to focus the portions of the beam that add together in phase onto the detector, and a beam stop, which is configured to block further portions of the beam that add together in antiphase from impinging on the detector.

9. Apparatus according to claim 4, wherein the first grating comprises a linear grating.

10. Apparatus according to claim 4, wherein the first grating comprises an array of concentric rings.

11. Apparatus according to claim 4, wherein the first grating is adapted to deflect the first portion of the beam that is incident on the DOE at an azimuthal angle $\phi$ so that it is optically combined with the second portion of the beam that is incident at a further azimuthal angle $\phi+\Delta\phi$, such that $\Delta\phi$ is substantially fixed over all azimuthal angles $\phi$.

12. Apparatus according to claim 4, wherein the first diffractive component has a thickness that varies over an area thereof, so as to impart a variable phase delay to the beam of scattered radiation that is incident over the area.

13. Apparatus according to claim 1, wherein the detector comprises a first detector, and the signal generated thereby comprises a first signal, and comprising a second detector, positioned to receive a part of the beam of scattered radiation not intercepted by the DOE and to generate a second signal responsive to the pan of the beam that it receives, wherein the signal processor is adapted to receive and compare the first and second signals in order to determine the autocorrelation value.

14. Apparatus according to claim 1, wherein the DOE is arranged so that a contribution to the scattered radiation due to a linear feature on the sample is suppressed in the product beam.

15. Apparatus according to claim 1, wherein the DOE is arranged so that a contribution to the scattered radiation due to a linear feature on the sample is enhanced in the product beam.

16. Apparatus according to claim 1, wherein the DOE is arranged so that a contribution to the scattered radiation due to a first feature located on a surface of the sample is enhanced in the product beam relative to the scattered radiation due to a second feature buried below the surface.

17. Apparatus according to claim 1, wherein the DOE is arranged so that a contribution to the scattered radiation due to a defect on a surface of the sample is enhanced in the product beam.

18. Apparatus according to claim 1, wherein the DOE is arranged so that a contribution to the scattered radiation due to a corner on the sample is suppressed in the product beam.

19. Apparatus according to claim 1, and comprising a scanning device, which is adapted to cause the irradiated spot to scan over a region of the sample, so as to enable the signal processor to determine the autocorrelation value at multiple points in the region.

20. Apparatus according to claim 19, wherein the signal processor is adapted to identify defects on the sample responsive to the autocorrelation value.

21. A method for optical inspection of a sample, comprising:
   irradiating a spot on the sample with coherent radiation;
   collecting dark field scattered radiation from the spot so as to form a beam of scattered radiation;
   positioning a diffractive optical element (DOE) to intercept the beam of scattered radiation, so as to deflect a first portion of the beam by a predetermined offset relative to a second portion of the beam, and then to optically combine the first portion with the second portion to generate a product beam;
   receiving the product beam and generating a signal responsive thereto; and
   processing the signal from the detector so as to determine an autocorrelation value of the product beam.

22. A method according to claim 21, wherein irradiating the spot comprises directing the radiation at the spot in a direction approximately normal to a surface of the sample, and wherein collecting the dark-field scattered radiation comprises collecting the scattered radiation so as to form a collimated beam with an annular cross-section.

23. A method according to claim 21, wherein collecting the radiation comprises collecting the radiation scattered from the spot at a grazing angle relative to a surface of the sample.

24. A method according to claim 21, wherein the DOE comprises a first diffractive component, having a first grating formed thereon, such that the first and second portions of the beam correspond to different diffraction orders of the grating.

25. A method according to claim 24, wherein the first portion of the beam comprises a first diffraction order of the grating, while the second portion of the beam comprises a zero diffraction order of the grating.

26. A method according to claim 24, wherein the DOE further comprises a second diffractive component, having a second grating formed thereon, so as to direct at least parts of the first and second portions of the beam in a common direction.

27. A method according to claim 26, wherein the second diffractive component is adapted and positioned, relative to the first diffractive component, so that the parts of the first and second portions of the beam that are directed in the common direction add together in phase.

28. A method according to claim 27, wherein receiving the product beam comprises focusing the portions of the beam that add together in phase onto a detector adapted to generate the signal, while blocking further portions of the beam that add together in antiphase from impinging on the detector.

29. A method according to claim 24, wherein the first grating comprises a linear grating.

30. A method according to claim 24, wherein the first grating comprises an array of concentric rings.

31. A method according to claim 21, wherein positioning the DOE comprises deflecting the first portion of the beam that is incident on the DOE at an azimuthal angle $\phi$ so that it is optically combined with the second portion of the beam that is incident at a further azimuthal angle $\phi+\Delta\phi$, such that $\Delta\phi$ is substantially fixed over all azimuthal angles $\phi$.

32. A method according to claim 21, wherein positioning the DOE comprises positioning a diffractive component having a thickness that varies over an area of the DOE, so as to impart a phase delay to the beam of scattered radiation that varies over the area.

33. A method according to claim 21, wherein generating the signal comprises generating a first signal responsive to the product beam, and comprising receiving a part of the beam of scattered radiation not intercepted by the DOE and to generating a second signal responsive to the pan of the beam, and wherein processing the signal comprises comparing the first and second signals in order to determine the autocorrelation value.

34. A method according to claim 21, wherein positioning the DOE comprises suppressing a contribution to the product beam due to the radiation scattered from a linear feature on the sample.

35. A method according to claim 21, wherein positioning the DOE comprises enhancing a contribution to the product beam due to the radiation scattered from a linear feature on the sample.

36. A method according to claim 21, wherein positioning the DOE comprises enhancing a contribution to the product beam due to the radiation scattered from a first feature located on a surface of the sample relative to the radiation scattered from a second feature buried below the surface.

37. A method according to claim 21, wherein positioning the DOE comprises enhancing a contribution to the product beam due to the radiation scattered from a defect on a surface of the sample.

38. A method according to claim 21, wherein positioning the DOE comprises suppressing a contribution to the product beam due to the radiation scattered from a corner on the sample.

39. A method according to claim 21, wherein irradiating the spot comprises scanning the spot over a region of the sample, and wherein processing the signal comprises determining the autocorrelation value at multiple points in the region.

40. A method according to claim 39, and comprising identifying defects within the region of the sample responsive to the autocorrelation value.

41. Apparatus for optical inspection of a sample, comprising:
a radiation source, adapted to irradiate a spot on the sample with coherent radiation;
collection optics, adapted to collect the radiation scattered from the spot so as to form a beam of scattered radiation;
a beam splitter splitting the beam of scattered radiation into a first beam and a second beam;
a diffractive optical element (DOE), which is positioned to intercept the first beam and is adapted to deflect a first portion of the first beam by a predetermined offset relative to a second portion of the first beam, and then to optically combine the first portion with the second portion to generate a product beam;
a first detector, positioned to receive the product beam and to generate a first signal responsive thereto;
a second detector, positioned to receive the second beam and to generate a second signal responsive thereto; and
a signal processor, which is coupled to receive and process the signals from the first and second detectors so as to determine presence or absence of defects on the sample.

42. The apparatus of claim 41, further comprising a filter situated to intercept said beam of scattered radiation.

43. The apparatus of claim 42, wherein said filter comprises central stop to block specular reflection.

44. The apparatus of claim 41, wherein the collection optics are adapted to collect the radiation scattered from the spot at a grazing angle relative to a surface of the sample.

45. The apparatus of claim 41, wherein the DOE comprises a first diffractive component, having a first grating formed thereon, such that the first and second portions of the beam correspond to different diffraction orders of the grating.

46. The apparatus of claim 45, wherein the first portion of the beam comprises a first diffraction order of the grating, while the second portion of the beam comprises a zero diffraction order of the grating.

47. The apparatus according to claim 45, wherein the DOE further comprises a second diffractive component, having a second grating formed thereon, so as to direct at least parts of the first and second portions of the beam in a common direction.

48. Apparatus according to claim 47, wherein the second diffractive component is adapted and positioned, relative to the first diffractive component, so that the parts of the first and second portions of the beam that are directed in the common direction add together in phase.

49. Apparatus according to claim 48, wherein the DOE comprises focusing optics, which are adapted to focus the portions of the beam that add together in phase onto the detector, and a beam stop, which is configured to block further portions of the beam that add together in antiphase from impinging on the detector.

50. Apparatus according to claim 45, wherein the first grating is adapted to deflect the first portion of the beam that is incident on the DOE at an azimuthal angle $\phi$ so that it is optically combined with the second portion of the beam that is incident at a further azimuthal angle $\phi+\Delta\phi$, such that $\Delta\phi$ is substantially fixed over all azimuthal angles $\phi$.

* * * * *